(12) United States Patent  
de Coninck

(10) Patent No.: US 8,486,117 B2
(45) Date of Patent: Jul. 16, 2013

(54) MULTI-AXIAL BONE PLATE SYSTEM

(75) Inventor: Cédric de Coninck, Cestas Gazinet (FR)

(73) Assignee: Stryker Spine (FR)

( * ) Notice: Subject to any disclaimer, the term of this patent is extended or adjusted under 35 U.S.C. 154(b) by 0 days.

(21) Appl. No.: 12/961,682

(22) Filed: Dec. 7, 2010

(65) Prior Publication Data

US 2011/0077691 A1 Mar. 31, 2011

Related U.S. Application Data

(62) Division of application No. 11/175,426, filed on Jul. 6, 2005, now Pat. No. 7,883,531.

(51) Int. Cl.
*A61B 17/80* (2006.01)
(52) U.S. Cl.
USPC ............ 606/286; 606/280; 606/288; 606/290
(58) Field of Classification Search
USPC ........ 606/280–299, 70, 71; 411/269; 403/370
See application file for complete search history.

(56) References Cited

U.S. PATENT DOCUMENTS

| 596,847 A | 1/1898 | Buchholtz | |
|---|---|---|---|
| 609,521 A | 8/1898 | Pennington | |
| 905,294 A * | 12/1908 | DeGroff et al. | ............... 411/269 |
| 1,063,397 A * | 6/1913 | Shults | ............................. 411/269 |
| 1,376,296 A * | 4/1921 | Snow | .............................. 411/269 |
| 4,673,376 A | 6/1987 | Fender | |
| 5,129,899 A | 7/1992 | Small et al. | |
| 5,234,431 A | 8/1993 | Keller | |
| 5,261,910 A | 11/1993 | Warden et al. | |
| 5,290,288 A | 3/1994 | Vignaud et al. | |
| 5,395,371 A | 3/1995 | Miller et al. | |
| 5,486,176 A | 1/1996 | Hildebrand et al. | |
| 5,591,166 A | 1/1997 | Bernhardt et al. | |
| 5,607,426 A | 3/1997 | Ralph et al. | |
| 5,607,428 A | 3/1997 | Lin | |
| 5,613,968 A | 3/1997 | Lin | |
| 5,676,666 A | 10/1997 | Oxland et al. | |
| 5,800,435 A | 9/1998 | Errico et al. | |
| 5,938,663 A | 8/1999 | Petreto et al. | |

(Continued)

FOREIGN PATENT DOCUMENTS

| FR | 2657775 | 8/1991 |
|---|---|---|
| FR | 2849766 | 7/2004 |

(Continued)

*Primary Examiner* — Jan Christopher Merene
(74) *Attorney, Agent, or Firm* — Lerner, David, Littenberg, Krumholz & Mentlik, LLP

(57) ABSTRACT

An orthopedic bone plate system having a bone plate for placement adjacent one or more vertebral bodies. The system further includes a locking element including a compression member and a fixation member wherein the compression member includes an aperture and at least one deformable portion. A bone fastener is also included in the present system which includes a bone engaging portion and a stem portion. The stem is capable of being slidably received within the aperture of the compression member while the locking member is capable of being received within an aperture of the bone plate. As the compression member is brought into proximity of a vertebral body along the longitudinal axis of the bone fastener, an increasing force is exerted against the fixation member and translated to the bone plate. The resultant force translated back to the fixation member to the compression member which causes the deformable portion of the compression member to clamp the bone fastener relative to the bone plate.

17 Claims, 7 Drawing Sheets

U.S. PATENT DOCUMENTS

| | | |
|---|---|---|
| 6,022,350 A | 2/2000 | Ganem et al. |
| 6,187,005 B1 | 2/2001 | Brace et al. |
| 6,287,309 B1 | 9/2001 | Baccelli et al. |
| 6,290,703 B1 | 9/2001 | Ganem et al. |
| 6,315,779 B1 | 11/2001 | Morrison et al. |
| 6,379,354 B1 | 4/2002 | Rogozinski |
| 6,379,357 B1 | 4/2002 | Bernstein et al. |
| 6,471,704 B2 | 10/2002 | Gertzbein et al. |
| 6,575,975 B2 | 6/2003 | Brace et al. |
| 6,585,738 B1 | 7/2003 | Mangione et al. |
| 6,641,583 B2 | 11/2003 | Shluzas et al. |
| 6,783,528 B2 | 8/2004 | Vincent-Prestigiacomo |
| 7,163,538 B2 | 1/2007 | Altarac et al. |
| 7,789,899 B2 | 9/2010 | Markworth et al. |
| 2002/0143328 A1 | 10/2002 | Shluzas et al. |
| 2002/0183747 A1 | 12/2002 | Jao et al. |
| 2002/0193795 A1 | 12/2002 | Gertzbein et al. |
| 2003/0045875 A1 | 3/2003 | Bertranou et al. |
| 2003/0045878 A1 | 3/2003 | Petit et al. |
| 2003/0105462 A1 | 6/2003 | Haider |
| 2003/0153919 A1 | 8/2003 | Harris |
| 2003/0187440 A1 | 10/2003 | Richelsoph et al. |
| 2004/0006342 A1 | 1/2004 | Altarac et al. |
| 2004/0087949 A1 | 5/2004 | Bono et al. |
| 2004/0177847 A1 | 9/2004 | Foley et al. |
| 2005/0010214 A1 | 1/2005 | Tassin |
| 2005/0234452 A1 | 10/2005 | Malandain |
| 2005/0234456 A1 | 10/2005 | Malandain |
| 2006/0149252 A1 | 7/2006 | Markworth et al. |
| 2008/0287994 A1 | 11/2008 | Perez-Cruet et al. |
| 2009/0281579 A1 | 11/2009 | Weaver et al. |

FOREIGN PATENT DOCUMENTS

| | | |
|---|---|---|
| WO | 88/03781 | 6/1988 |
| WO | 9400066 | 1/1994 |
| WO | 9535067 | 12/1995 |
| WO | 03/068088 | 8/2003 |
| WO | 2005013840 | 2/2005 |

* cited by examiner

MULTI-AXIAL BONE PLATE SYSTEM

CROSS-REFERENCE TO RELATED APPLICATION

This application is a divisional of U. S. application Ser. No. 11/175,426, filed on Jul. 6, 2005, now U.S. Pat. No. 7,883,531, the disclosure of which is incorporated herein by reference.

BACKGROUND OF THE INVENTION

The present invention relates generally to an orthopedic implant assembly system and in particular to a multi-axial bone plate system.

Orthopedic implant assembly systems having a multi-axial bone plate are known in the art and include at least two pedicular screws anchored in adjacent vertebrae to be treated and a connecting plate designed to connect the screw heads together in a rigid manner. Previous references disclose a system of this kind in which each pedicular screw has a hexagonal section part for inserting the screw into the bone and on top of which is a threaded shank. The plate has a plurality of oblong openings through which the various threaded shanks can be inserted and an open groove on its bottom face to prevent rotation of the hexagonal part of each pedicular screw.

Each pedicular screw is associated with a stirrup through which the threaded shank of the screw also passes and which straddles the top of the plate. Finally, a nut is screwed onto the threaded shank to trap and immobilize the plate with the stirrup on top of it, between it and the hexagonal portion of the screw.

Further, known systems include at least two pedicular screws and a connecting plate for linking screws together in essentially a rigid manner. Each screw has a bone anchor threaded part, a non-circular section head, and a threaded end shank adapted to cooperate with a nut. The plate has at least one opening adapted to have the threaded end shank of the screw pass through it and be trapped between the screw head and the nut. Raised patterns are provided on the top face of the plate and on the bottom face of the stirrup to prevent longitudinal sliding of the plate relative to the screw. A locking member is also provided for preventing relative angular movement between the heads of the screws and the connecting plate. The locking member is adapted to be inserted between the plate and the screw head and includes a bar through which the threaded end shank of the screw passes. The locking member further includes a first locking cooperation of shapes with the screw head and a second cooperation of shapes with the plate.

Although these systems are generally satisfactory, they nevertheless have certain drawbacks. Specifically, in certain systems, raised patterns have to be provided to prevent sliding because the plate and the stirrup cooperate via two plane faces in compression. Absence of the raised patterns would lead to the risk of entirely unacceptable relative movement of the vertebrae. The machining required to create these raised patterns significantly increases the mean cost of the plates and the stirrups.

Additionally, the raised patterns can impede fine adjustment of the system. For example, there are only a particular number of discrete mutual positions of the plate and the stirrup, i.e., a particular number of discrete distances between the screws. Moreover, if the nut is overtightened before the final tightening, lateral sliding of the plate and the stirrup during adjustment may be impeded.

Some of the drawbacks associated with other designs include that the first locking cooperation and second cooperation of shapes with the plate forbid and restrict plate movement in an anterior and posterior direction once the pedicle screw has been rested against the plate member.

Additionally, most plate systems include a bone fastener with a threaded end extended from the vertebral body. In order to lock the screw relative to the plate, a nut must be used in combination with the screw. The problem associated with this design is that if the screw is not placed at the correct depth within the vertebral body, the assembly must be disassembled in order to either increase or decrease the depth of the screw in the vertebrae. An additional problem results from this action due to the fact that once the screw has been placed too deep within the vertebral body, the screw might be less securely locked within the vertebral body when the screw is backed out and placed in its correct position.

Other shortcomings of known systems include angled orientations in the sagittal direction are not permitted due to the shape of the locking cooperation members.

SUMMARY OF THE INVENTION

In accordance with one or more embodiments of the present invention, an orthopedic bone plating system includes a bone plate for placement adjacent one or more vertebral bodies. The bone plate has an aperture extending along a longitudinal axis of the bone plate.

The assembly further includes a locking element having a compression member and a fixation member wherein the compression member has an aperture and at least one deformable portion. The assembly is connected to a vertebral body with the help of a bone fastener having a longitudinal axis. The bone fastener further includes a stem and a bone-engaging portion. The stem of the bone fastener may be slidably received within the aperture of the compression member. As the stem is being received by the compression member, the compression member may be brought into proximity of a vertebral body along the longitudinal axis of the bone fastener and create an increasing force which is exerted against the fixation member. A resulting force causes the fixation member to exert a pressure against the bone plate and translate a second resultant force back through the fixation member to the compression member causing the deformable portion of the compression member to clamp onto the bone fastener thereby locking the assembly together.

The compression member and fixation member may be separate elements wherein the fixation member includes an aperture for receiving the compression member. Furthermore, the compression member and fixation member may have mateable threads which are screwed together as the compression member is brought into proximately of the vertebral body.

The fixation member may further include a tapered aperture extending therethrough. Additionally, the bone fastener may be smooth.

The orthopedic bone plate system may include a channel for receiving the fixation member, which permits the fixation member to slide relative to the bone plate. The channel being located within the bone plate. Furthermore, the fixation member may include at least one key and the bone plate may include at least one keyway wherein the key may be received by the keyway. In at least one embodiment, the keyway may have a height that is greater than the height of the key in order to permit an angled orientation of the fixation member relative to the bone plate.

In an additional embodiment of the present invention, an orthopedic bone plate implant system is provided having a plate member which may be placed adjacent and along one or more of the vertebral bodies. The plate member includes an aperture extending therethrough. The assembly also includes a split sleeve having a central aperture and a slot extending from an exterior surface of the split sleeve to the aperture. The slot permits the expansion and contraction of the aperture of the split sleeve. The split sleeve is sized to be received within the aperture of the plate member.

The channel portion may extend substantially the entire longitudinal direction of the plate and either come to a tapered end or abrupt end. Furthermore, the channel portion itself may also include a guide rail that receives a lateral pin extending from an exterior of the split sleeve. The lateral pin is placed and dimensioned on the split sleeve to be received by the guide rail when the split sleeve is placed in the channel portion of the plate member.

The split sleeve may have two parallel flat walls and two opposite curved walls.

In one embodiment of the present invention, the parallel flat walls may include the lateral pins of the split sleeve.

The bone fastener may have an end portion that is either smooth, concaved inwards or outwards relative to the vertebral body. The bone fastener may further include a recess for cooperating with the tool. The recess may be in the form of a hexagon, a slot or various other recesses and projections which can be made into a tool.

A bottom portion of the expansible screw may include at least one slit extending vertically to allow the compression or expansion of a portion of the expansible screw.

Furthermore, the expansible screw may include a ridge which overhangs at least partly the split sleeve. The ridge may further be defined in that it has at least two flat surfaces on its sidewall. The split sleeve may include a threaded portion and the expansible screw may include a second threaded portion wherein the two threaded portions are able to be screwed to one another.

In an alternate embodiment, the plate member of the orthopedic input may include slots or ridges. Additionally, the split sleeve may have a central aperture which has an interior with a greater circumference at the top of the interior as you get to the bottom of the interior. Furthermore, the expansible screw having an aperture within may include an exterior with a bottom portion angled so as to increase in size.

The method of operation of the present invention may include the steps of providing a plate member, a bone fastener and a locking element as described herein. The bone fastener may first be engaged to a vertebral body and then the stem of the bone fastener slidably receiving the plate member and the locking element about its circumference so that the stem is located within the apertures of the plate and the locking element respectively. The locking element may include a compression member and a fixation member. As the compression member is brought into proximity of the vertebral body along the longitudinal axis of the bone fastener, the compression member causes an increasing force to be exerted against the fixation member which in response places pressure against the plate member until a resultant force is translated back through the two members and causes the deformable portion of the compression member to clamp the bone fastener relative to the bone plate.

The method of fixing one or more vertebral bodies in a desired relationship may further include adjusting the position of the bone fastener after sliding the plate member over the stem of the bone fastener.

A bone fastener is also included for connecting the plate member to a vertebral body. The fastener may include a first end portion engageable with the vertebral body and a second end portion capable of extending through the aperture of the split sleeve.

A final component of the assembly is an expansible screw having an opening extending therethrough. The opening is sized to receive the second end portion of the fastener and further includes a top portion and a bottom portion. The bottom portion of the screw is capable of expanding and contracting about a central axis of the screw.

BRIEF DESCRIPTION OF THE DRAWINGS

FIG. 6b is a cross-sectional view of the split sleeve of FIG. 6a;

FIG. 7b is a cross-sectional view of the expandable screw of FIG. 7a;

DETAILED DESCRIPTION

Figure 1:
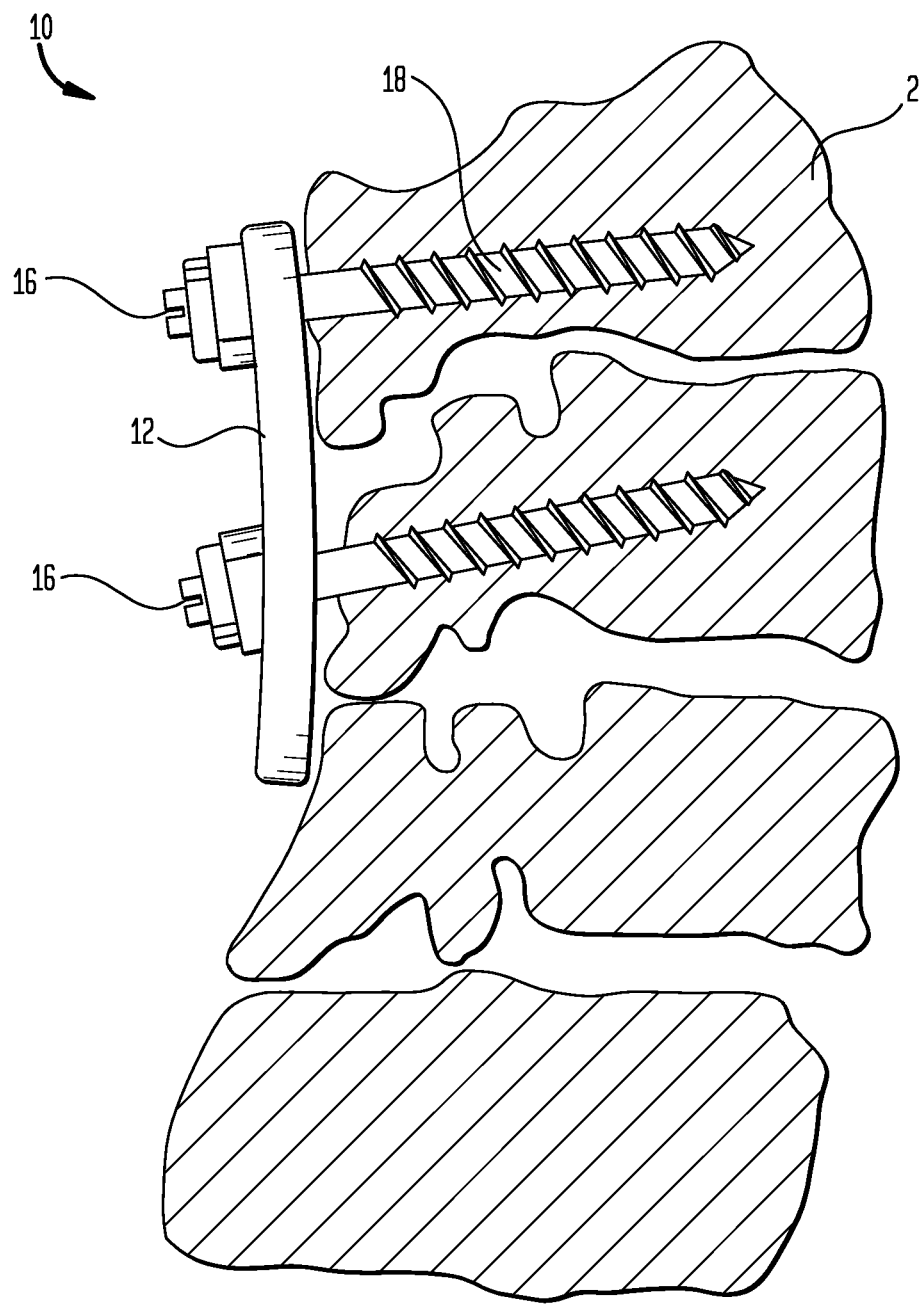
FIG. 1 is a schematic drawing illustrating an embodiment of the orthopedic implant of the present invention implanted in a vertebrae.

For the purposes of promoting and understanding the principles of the present invention, reference will now be made to the embodiment illustrated in the drawings and specification language will be used to describe the same. Nevertheless, by those skilled in the art, it will be understood that no limitation of the scope of the present invention is thereby intended, and further changes in the illustrated device may be made without deviating from the scope of the present invention.

As shown in FIG. 1, the spinal implant system 10 of the present invention includes a plate 12, an expansible locking screw 16 and a bone fastener 18. As shown in the figures, bone fasteners 18 function to anchor plate 12 to vertebral bodies 2 and may be orientated at an angle with regard to the vertebral body.

Figure 2:
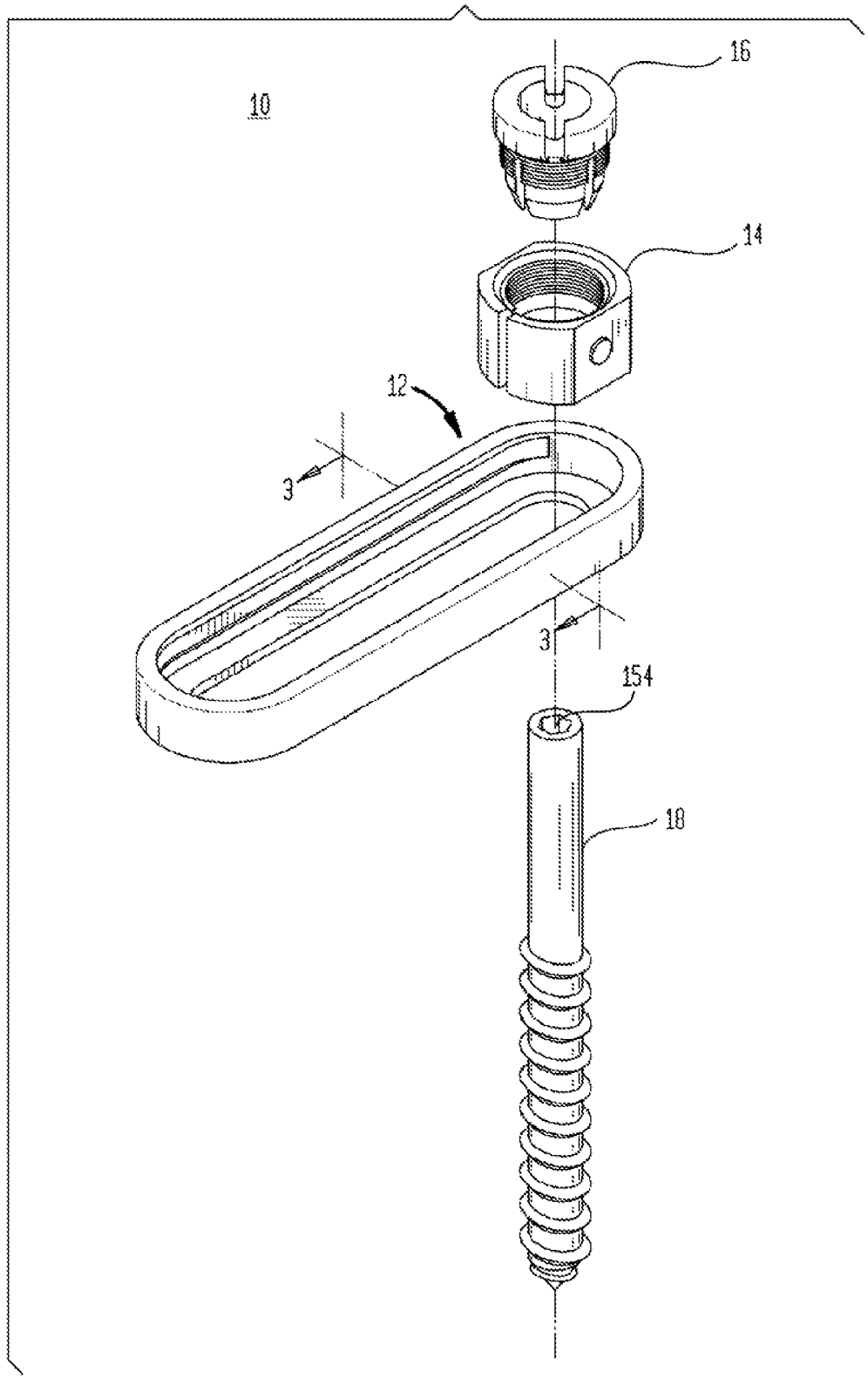
FIG. 2 is an exploded perspective view of one embodiment of the system of the present invention.
Figure 3:
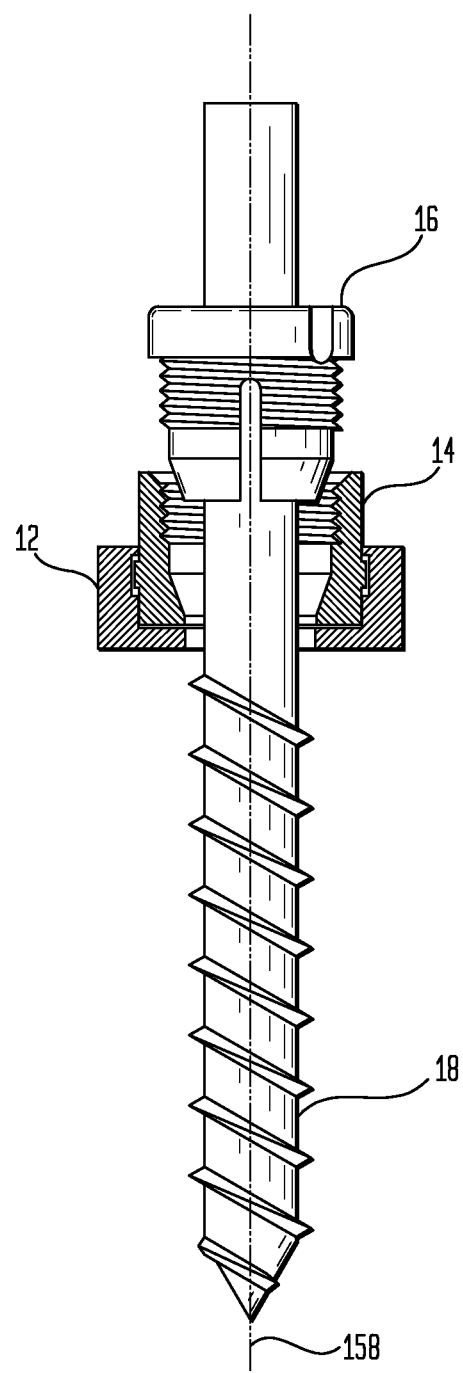
FIG. 3 is a sectional view of the embodiment illustrated in FIG. 2 partly assembled and taken along line 3-3 in FIG. 2 and viewed in direction of the arrows.

FIG. 2 details the assembly of the parts of FIG. 1 employed in the spinal implant system 10. In a preferred embodiment, the spinal implant system 10 includes an elongate member such as plate 12, expansible screw 16, bone fastener 18 and split sleeve 14. Although the preferred embodiment illustrated in the figures is shown with only one plate 12 and bone fastener 18 and related elements, differing numbers of any of these elements may be utilized without departing from the scope of the present invention. For example, a plurality of plates 12 can be used in conjunction with each other, or a greater or lesser number of bone fasteners 18 may be used depending upon the configuration of the elongate member, the medical problem to be addressed and/or any other factors. The present invention contemplates having at least the same amount of split sleeves 14, expansible screws 16 and bone fasteners 18. Furthermore, the present invention contemplates each plate 12 will be used with at least a single bone screw 18 and related devices; however, each plate 12 is capable of receiving a plurality of split sleeves 14, expansible screws 16 and bone fasteners 18 without deviating from the scope of the present invention.

Referring now to FIGS. 2, 3, 4a and 4b, there is shown a preferred embodiment of plate 12. Plate 12 preferably has a generally rounded-rectangular or oval shape, an upper surface 30, a lower surface 32, a proximal end 31 and a distal end 33. Additionally, plate 12 has two opposing sides, right rail 13 and left rail 15. Right rail 13 and left rail 15 may be substantially mirror images of one another. Plate 12 further includes elongate aperture 36 extending along the longitudinal axis 34 of plate 12 from upper surface 30 to lower surface 32 and from end 31 to end 33. Elongate aperture has a generally open geometry enabling split sleeve 14, expansible screw 16 and bone fastener 18 to be placed at any number of axial positions within elongate aperture 36. Elongate aperture 36 generally has a non-uniform geometry about a central axis 35 which extends perpendicularly to the plane of plate 12.

Figure 4A:
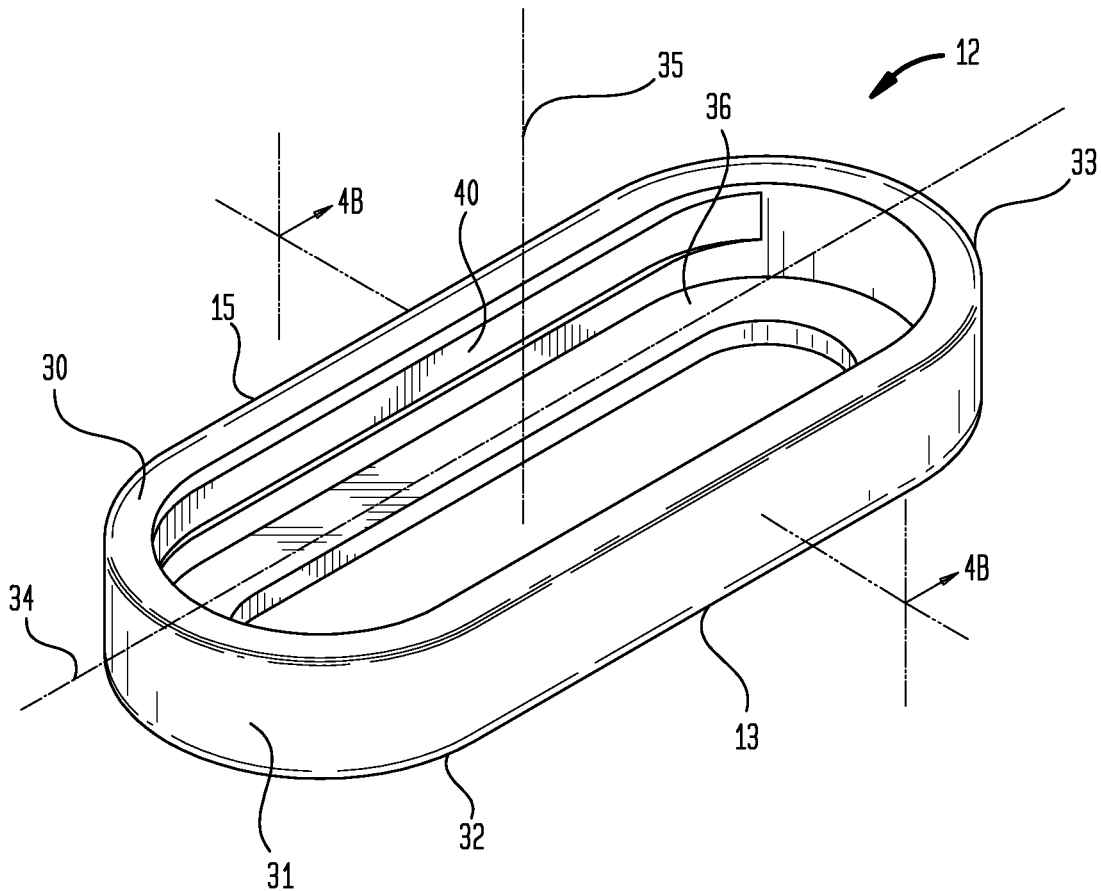
FIG. 4a is a perspective view of an elongate plate used in one embodiment of the present invention.
Figure 4B:
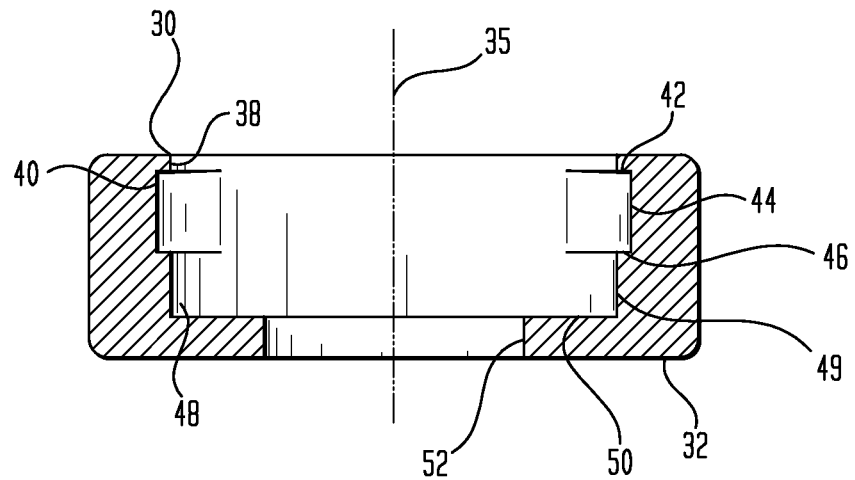
FIG. 4b is a cross-sectional view of a plate used in one embodiment of the present invention.

In a preferred embodiment, right rail 13 and left rail 15 surround elongate aperture 36 of plate 12 and include an upper wall 38 adjacent to upper surface 30. The geometry of left rail 13 and upper rail 15 of aperture 36 further include a key way or groove 40 adjacent to upper wall 38 composed of median ceiling 42, median portion 44 and median ridge 46. A lower portion 48 of rails 13 and 15, adjacent to key way 40, includes a lower surface 50 adjacent to lower wall 49 and sidewall 52 adjacent to lower ridge 50, concludes the remaining exterior geometry of elongate aperture 36. In one embodiment, elongate aperture 36 has substantially the same geometry extending from the proximal end 31 to the distal end or the previously mentioned ridge portions and rails may either abruptly halt or in a preferred embodiment may linearly transition into a smooth geometry at the distal and proximal ends as shown in FIG. 4a.

Plate 12 is of sufficient length to bridge more than one vertebrae, as shown in FIG. 1, for which stabilization is required, and it will be appreciated, various dimensions of the plate and its features exist, all within the scope of the present invention. For example, the plate 12 may be substantially planar as shown in FIG. 2 or have a concave shape as shown in FIG. 1.

The plate 12, as well as the other elements of the assembly, is preferably made from a biologically inert material, for example, any metal customarily used for surgical devices and particularly those used for bone screws and pins, such as titanium or stainless steel. Other suitable materials include, but are not limited to, alloys, composite materials, ceramics or carbon fiber materials.

Figure 5:
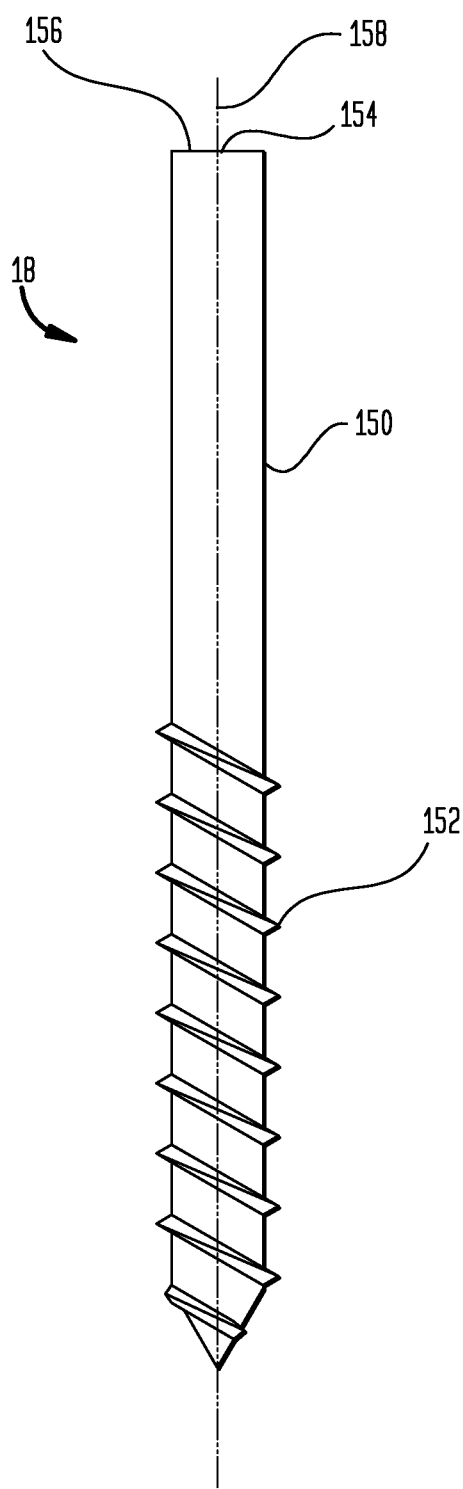
FIG. 5 is a front perspective view of a bone fastener used in one embodiment of the present invention.

With reference to FIG. 5, there is shown a preferred embodiment of a bone fastener 18. Bone fastener 18 is in the shape of a pedicle screw; however, various other fasteners may be utilized including bone hooks. Preferably, bone fastener 18 has a threaded end 152 for anchoring the fastener into a vertebra or similar bone structure and an opposing stem end 150. In a preferred embodiment, stem end 150 is smooth. Bone fastener 18 may further include recess 154 to enable bone fastener 18 to be screwed into a vertebrae using a screw driver, wrench, allen key or similar tool. Recess 154 may be in the form of a hexagon as shown in the figures or alternatively, may be a slot or other shapes which allow the tools previously mentioned to mate to the bone fastener 18 and screw the bone fastener 18 into a vertebral body. Smooth stem 150 is preferably sized to be able to be slidably received by expansible screw 16, detailed in FIGS. 7a and 7b, specifically aperture 124 of expansible screw 16 as will be described below. Bone fastener 18 may also include upper end section 156, which may have a substantially flat end surface area as shown in FIG. 5. However, in an alternate embodiment, upper section 156 may also have a spherical configuration either concave or convex relative to threaded end 152.

Referring now generally to FIGS. 2, 3, 6a and 6b, there is shown a preferred embodiment of a split sleeve 14. Split sleeve 14 may have a generally rounded-square or oval shape. Split sleeve 14 may include a first flat side 60, and opposing second flat side 62, a first arcuate side 64 and an opposing second arcuate side 66. Sides 64 and 66 could be of any shape, however, sides 60, 62 preferably permit split sleeve 14 to slide within aperture 36 without rotating. Split sleeve 14 may further include an upper surface 68 and a lower surface 70 along with aperture 72, extending therebetween. Aperture 72 generally has a non-uniform geometry about central axis 74. The first side 60 and second side 62 may include keys 76 and 78 which engage key ways 40 on rails 13 and 15 of the plate 12, respectively. Although a description of only one key will be detailed with reference to key 76, it should be realized that key 78 may be substantially similar to key 76 having all the same features. Key 76 protrudes from second side 62 and includes top ledge 80 and lower ledge 82 extending horizontally from second side 62. Side 84 adjacent to both top ledge 80 and lower ledge 82 extends between the two ledges. Key 76 may be sized and located on second side 62 so when split sleeve 14 is placed into elongate aperture 36 of plate 12, pin 76 is housed within key way 40 as defined by side 84. Keys 76 and 78 may have a height slightly less than the height of key way 40 to permit split sleeve 14 to slide freely along key way 40 of plate 12. Furthermore, the reduced height of key 76 enables split sleeve 14 to have an angled orientation relative to plate 12, in the sagittal plane. In the preferred embodiment, keys 76, 78 extend only part way along sides 60, 62 but could extend the entire length.

Split sleeve 14 further includes through-slot 102 vertically extending from upper surface 68 to lower surface 70. Slot 102 is further defined in that it extends horizontally from the exterior of split sleeve 14 to aperture 72. The outer circumference of split sleeve 14 is substantially continuous except for through-slot 102. Through-slot 102 permits split sleeve 14 to expand and compress horizontally thereby increasing or decreasing the diameter of aperture 72. Split sleeve 14 may be compressed about slot 102 to allow insertions of keys 76, 78 into key way 40.

Figure 6A:
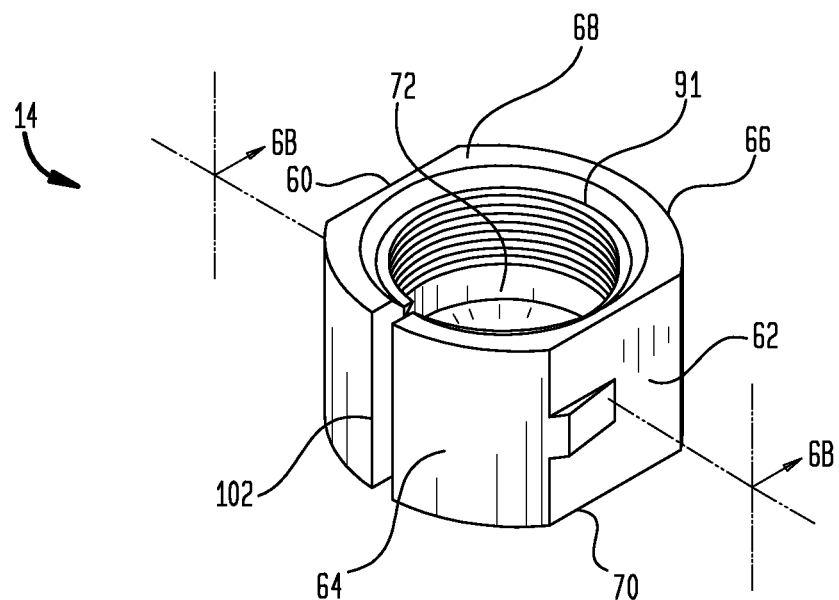
FIG. 6a is a perspective view of a split sleeve used in one embodiment of the present invention.
Figure 6B:
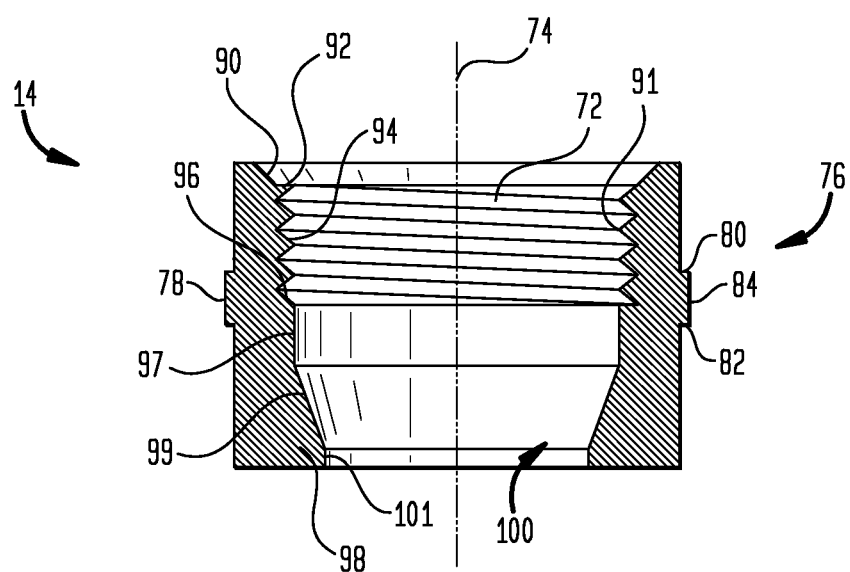

As previously mentioned, aperture 72 has a non-uniform geometry extending between upper surface 68 to lower surface 70 of split sleeve 14. Specifically, inner wall 90 is adjacent to upper surface 68. Inner wall 90 may have a tapered design as shown in FIG. 6B to better receive expansible screw 16, as will be described below. A first ridge 92 extends from inner wall 90 towards central axis 74, with median wall 94 extending downward towards lower surface 70 adjacent to first ridge 92. A second ridge 96 is adjacent to median wall 94 and extends toward central axis 74 while lower wall 98 is adjacent to second ridge 96. Inner wall 90 includes threads 91 which may be mated to the threads of the expansible screw 16 described herein after. Lower wall 98 may include vertical wall 97 and tapered skirt 99 along with edge 101. Inner wall 90, first ridge 92, median wall 94, second ridge 96 and lower wall 98 all combine to define female cone 100.

Split sleeve 14 is placed within elongate aperture 36 of plate 12 when assembling the spinal implant assembly 10. In this position, lower surface 70 of split sleeve 14 is rested on or slightly above lower ridge 50 of plate 12 and as previously mentioned, pins 76 and 78 are located within key way 40 at the right rail 13 and the left rail 15 of the plate 12. Split sleeve 14 is sized to move freely along plate 12 and permit a possible angled orientation of the split sleeve with respect to plate 12 in the sagittal plane. Thus, preferably, the height of split sleeve 14 is less than the distance from the upper surface 30, to lower ridge 50. Preferably, in a relaxed state, split sleeve 14 has a width less than the distance between opposing rails 13 and 15 of aperture 36 of plate 12.

Figure 7A:
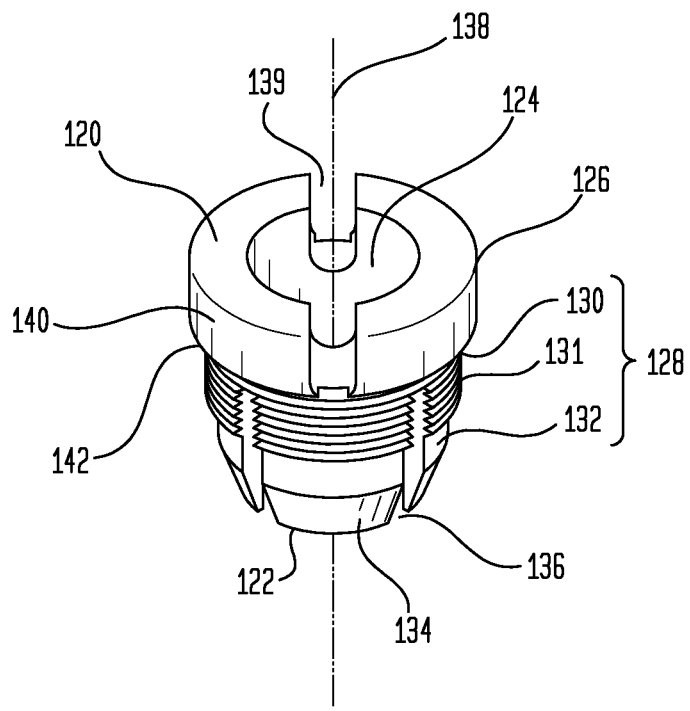
FIG. 7a is a perspective view of an expandable screw used in one embodiment of the present invention.
Figure 7B:
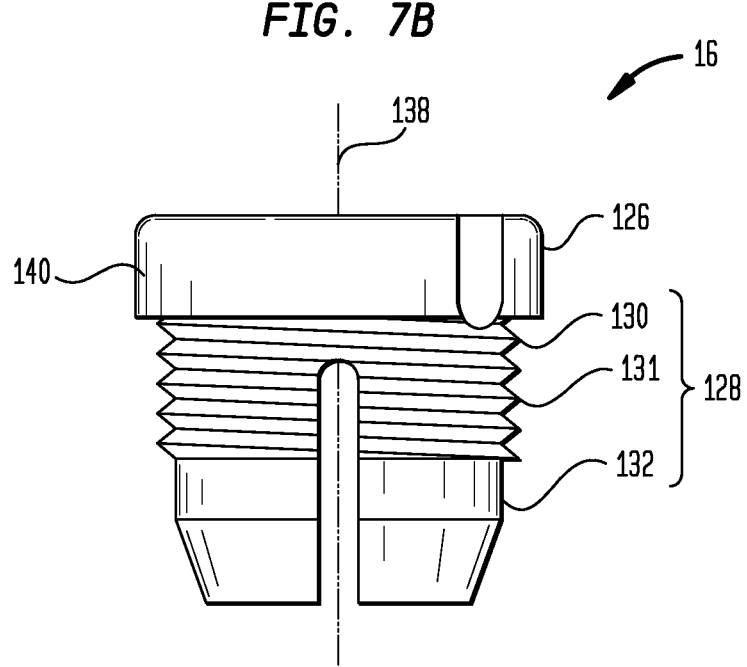

Referring now to FIGS. 7a and 7b, there is shown a preferred embodiment of the expansible screw 16. The expansible screw 16 includes upper surface 120, lower surface 122 and aperture 124 extending therebetween upper surface 120 and lower surface 122. Expansible screw 16 further includes cap section 126 and deflectable male cone section 128. Axially extending portion 130 includes threads 131 which are engageable with threads 91 on split sleeve 14. Male cone section 128 further includes, extending downward from ridge 132, individual fingers 134 with slits 136 therebetween each individual finger 134. Preferably, fingers 134 are tapered inwards so as to be slidably received by lower wall 90 of split sleeve 14. Male cone 128 of expansible screw 16 is designed so as to be able to receive fastener 18 and is geometrically constant throughout aperture 124. However, as a force is exerted horizontally relative to central axis 138 of expansible screw 16, male cone 128 is capable of compressing either inwardly or expanding outwardly in the same direction of the force applied. Cap section 126 of expansible screw 16 includes not only upper surface 120 but also grip surface 140 and overhang 142 and may also include opposing slots 139 for cooperating with a tool. Furthermore, aperture 124 also extends through cap section 126 thereby creating a continuous aperture through expansible screw 16.

In a method of use, once bone fastener 18 has been coupled with or fastened to a vertebral body, plate 12 along with split sleeve 14 is placed over smooth stem 150 of bone fastener 18. First split sleeve 14 may be placed within aperture 36 of plate 12. Then, by aligning upper section 156 of bone fastener 18 to aperture 72 of split sleeve 14, split sleeve 14 and plate 12 are slidably received by stem 150. Since bone fastener 18 is a substantially cylindrical body having a center axis, this alignment may be accomplished by aligning central axis 74 of split sleeve 14 to the center axis 158 of bone fastener 18. Bone plate 12 and split sleeve 14 are then freely moveable in a vertical direction relative to bone fastener 18 and specifically an anterior-posterior direction.

In order to lock the various components of the spinal implant assembly 10 together, expansible screw 16 must be screwed into split sleeve 14. This is accomplished by first aligning aperture 124 of expansible screw 16 with upper section 156 of bone fastener 18. Once again, since stem 150 of bone fastener 18 is substantially cylindrical and has a radial central axis 158, central axis 138 of expansible screw 16 may be aligned with the radial central axis 158 of the bone fastener 18.

Aperture 72 of split sleeve 14 is sized so as to be able to accept expansible screw 16 and bone fastener 18 at opposing ends. Furthermore, expansible screw 16 engages threads 91 within aperture 72 of split sleeve 14 and the two are screwed together such that the tapered portions of each engage one another. This causes an outward horizontal force against split sleeve 14 and an inward force on deflectable fingers 134. The fingers 134 grip the stem 156 of the bone fastener 18 as they are constricted inwards. This is due to the fact that male cone 128 of expansible screw 16 is wedged shaped, i.e., having a narrower lower portion as compared to its upper portion. Through-slot 102 of split sleeve 14 permits the expansion of split sleeve 14 in the horizontal direction. As split sleeve 14 is forced to expand, first side 60 begins to apply pressure against upper wall 38 and lower wall 49 of the plate 12. Key 78 may contact median portion 44 of key way 40 located on plate 12. Similarly, at the opposing end, second side 62 also applies pressure against upper wall and lower wall 49 as well as the fact that key 76 may contact median portion 44 of guide rail 40 of plate 12. Thus, as a horizontal force in a direction away from central axis 74 of split sleeve 14 is placed on the interior of the split sleeve 14, the split sleeve 14 expands horizontally increasing the size of through-slot 102 until the rails 13 and 15 of elongated aperture 36 of plate 12 apply a reactive force against the walls of split sleeve 14 thus locking the split sleeve in place.

Once split sleeve 14 has reached its maximum expansion capability, further axial movement of expansible screw 16 causes it to lock on to screw 18. Since expansible screw 16 is further translated downward, and split sleeve 14 can no longer expand, the reactive force caused by the plate 12 translated through split sleeve 14 begins to compress fingers 134 of expansible screw 16. This causes fingers 134 to constrict about smooth stem 150 of bone fastener 18 locking the bone fastener relative to the plate.

In a locked position, cap 126 of expansible screw 16, specifically overhang 142 of expansible screw 16 may abut upper surface 68 of split sleeve 14. Thus, male cone 128 is completely housed in aperture 72 of split sleeve 14.

The rotation of expansible screw 16 thus causes the plate to lock relative to the bone fastener 18. The stem 150 of bone fastener 18 may have a smooth surface to allow easy adjustment after plate 12 has been positioned and assembled, thus overcoming the disadvantage of threaded end fasteners. The surgeon may easily change the bone screw position engaged with the vertebrae by loosening expansible screw 16 and sliding the assembly in either an anterior/posterior direction or inferior/superior direction. Afterwards, the assembly may be locked again by tightening expansible screw 16. This avoids the problem of having to disassemble all the elements from one another in order to adjust only certain elements.

Other embodiments not shown in the illustrated figures may include single elongated aperture 36 being divided into a plurality of apertures by cross-members extending between opposing rails 13 and 15 of plate 12 substantially perpendicular to longitudinal axis 34. The cross-members would have to be sufficiently separated from one another as well as from proximal end 31 and distal end 33 to permit split sleeve 14, expansible screw 16 and bone fastener 18 to be placed within the shortened apertures and still be locked together relative to plate 12.

Although the present invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An orthopedic bone plate implant system, comprising:
    a plate member for placement adjacent and along one or more vertebral bones, having an aperture extending along a longitudinal axis;
    a split sleeve having a central aperture extending therethrough, said split sleeve having a slot extending from an exterior surface of said split sleeve to said aperture; said slot permitting the expansion and contraction of said aperture of said split sleeve, wherein said exterior surface is dimensioned to be received within said aperture of said plate member;

a bone fastener having a longitudinal axis for connecting said plate member to a vertebral body, said fastener having a first end portion engageable with said vertebral body and a second end portion capable of extending through said aperture in said split sleeve; and a screw having an opening extending therethrough, said opening sized so as to be able to receive said second end portion of said fastener therethrough while said screw advances relative to said bone fastener along said longitudinal axis of said bone fastener, said screw further including a top portion and a bottom portion, said bottom portion capable of expanding and contracting about a central axis of said screw.

2. The orthopedic bone plate implant system according to claim 1 wherein said plate member includes a channel portion that extends substantially the entire longitudinal direction of said plate member, said channel portion being sized so as to be able to receive such split sleeve.

3. The orthopedic bone plate implant system according to claim 2 wherein said channel portion of said plate member includes a guide rail, said split sleeve includes at least one lateral pin extending from an exterior of said split sleeve, said at least one lateral pin being placed and dimensioned on said split sleeve so as to be able to be received by said guide rail when said split sleeve is placed in said channel portion of said plate member.

4. The orthopedic bone plate implant system according to claim 3, wherein said split sleeve has two parallel flat walls and two opposite curved walls, and wherein said at least one lateral pin is located on said parallel flat walls.

5. The orthopedic bone plate implant system according to claim 1 wherein said split sleeve has two parallel flat walls and two opposite curved walls.

6. The orthopedic bone plate implant system according to claim 1, wherein said second end portion of said fastener is smooth.

7. The orthopedic bone plate implant system according to claim 1, wherein said second end portion of said fastener includes a recess for cooperating with a tool.

8. The orthopedic bone plate implant system according to claim 1, wherein said bottom portion of said screw includes at least one slit extending vertically.

9. The orthopedic bone plate implant system according to claim 1, wherein said top portion of said screw includes a ridge to overhang a portion of said split sleeve when split sleeve and said expansible screw are interconnected.

10. The orthopedic bone plate implant system according to claim 1, wherein said top portion of said screw includes a feature for cooperating with an insertion tool.

11. The orthopedic bone plate implant system according to claim 1, wherein said split sleeve includes a threaded portion and said screw includes a second threaded portion, wherein said first and second threaded portions are capable of being screwed to one another.

12. An orthopedic implant system, comprising:

a plate member for placement adjacent and along one or more bones and having a longitudinal axis, said plate member having a slot substantially parallel to said longitudinal axis, said slot surrounded by walls defining a channel extending along said longitudinal axis of said plate member, said walls including a key way extending along said channel of said plate member;

a split sleeve having a central aperture including a slot extending from an exterior of said split sleeve to said central aperture, said split sleeve having two substantially opposing exterior sides sized so as to be able to slide along said channel of said plate member, each side including a key positioned and sized so as to be received by and slide along said key way of said plate member when said split sleeve is in its normal position, said split sleeve including an interior having a smaller circumference at the bottom of said interior compared to the circumference at the top of said interior;

an expansible screw, said expansible screw having a first aperture extending longitudinally therethrough and an exterior bottom portion angled so as to increase in size as it extends upwardly, said angled exterior bottom portion of said expansible screw being adapted to engage said interior of said split sleeve; and a fastener, said fastener having a bone engaging portion at its bottom end and a smooth stem portion at its top end, said fastener extending through said aperture of said expansible screw, said aperture of said split sleeve, and said slot of said plate member.

13. The orthopedic bone plate implant system according to claim 12, wherein said split sleeve includes a threaded portion and said expansible screw includes a second threaded portion, wherein said first and second threaded portions are capable of engaging one another.

14. The orthopedic bone plate implant system according to claim 12, wherein said sides of said split sleeve are flat and substantially parallel to each other.

15. The orthopedic bone plate implant system according to claim 14, wherein said split sleeve has two opposite curved walls extending between said sides.

16. The orthopedic bone plate implant system according to claim 12, wherein said expansible screw has a top portion sized so as to overhang a top surface of said split sleeve.

17. The orthopedic bone plate implant system according to claim 16, wherein said top portion of said expansible screw includes a feature for cooperating with an insertion tool.

* * * * *

UNITED STATES PATENT AND TRADEMARK OFFICE
CERTIFICATE OF CORRECTION

PATENT NO. : 8,486,117 B2  
APPLICATION NO. : 12/961682  
DATED : July 16, 2013  
INVENTOR(S) : Cédric de Coninck Page 1 of 1

It is certified that error appears in the above-identified patent and that said Letters Patent is hereby corrected as shown below:

Title page, item 57 abstract, line 14-15, "resultant force translated back" should read -- resultant force is translated back --.
In the specification
Column 5, line 17, "aperture has" should read -- aperture 36 has --.
Column 5, line 26, "left rail 13" should read -- right rail 13 --.
Column 5, line 26, "upper rail 15" should read -- left rail 15 --.
In the claims
Column 9, line 48, Claim 9, "when split" should read -- when said split --.

Signed and Sealed this  
Third Day of November, 2015

Michelle K. Lee  
*Director of the United States Patent and Trademark Office*